United States Patent
Stubbs et al.

(10) Patent No.: US 7,413,559 B2
(45) Date of Patent: *Aug. 19, 2008

(54) GAS FLOW TROCAR ARRANGEMENT

(75) Inventors: Jack B. Stubbs, Waynesville, OH (US);
Ronald J. Thompson, Ft. Thomas, KY (US); George A. J. Hartman, Waynesville, OH (US); Donald N. Halgren, Manchester, MA (US); Michael J. Campbell, Louisville, KY (US)

(73) Assignee: SurgiQuest, Incorporated, Orange, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/517,751

(22) Filed: Sep. 8, 2006

(65) Prior Publication Data

US 2007/0088274 A1 Apr. 19, 2007

Related U.S. Application Data

(60) Division of application No. 10/739,872, filed on Dec. 18, 2003, now Pat. No. 7,285,112, which is a continuation-in-part of application No. 10/441,149, filed on May 17, 2003, now Pat. No. 7,182,752, said application No. 10/739,872.

(60) Provisional application No. 60/461,149, filed on Apr. 8, 2003.

(51) Int. Cl.
*A61M 5/178* (2006.01)
(52) U.S. Cl. .................. 604/167.01; 604/23; 604/26; 604/500; 604/506; 604/164.01; 606/167

(58) Field of Classification Search ............. 604/23–26, 604/43–45, 500, 506, 507, 272, 164.01, 164.02, 604/167.01, 167.02, 167.03, 167.04, 167.05, 604/167.06; 128/898; 606/167
See application file for complete search history.

(56) References Cited

U.S. PATENT DOCUMENTS

| | | | |
|---|---|---|---|
| 6,309,382 B1 * | 10/2001 | Garrison et al. ................ 606/1 |
| 6,685,665 B2 * | 2/2004 | Booth et al. .................. 604/26 |
| 6,905,489 B2 * | 6/2005 | Mantell et al. ............... 604/506 |
| 2004/0199121 A1 | 10/2004 | Wenchell et al. | |
| 2005/0010164 A1 * | 1/2005 | Mantell ....................... 604/26 |

FOREIGN PATENT DOCUMENTS

| EP | 1 188 415 A | 3/2002 |
|---|---|---|
| WO | WO 96/01132 A | 1/1996 |

OTHER PUBLICATIONS

Invitation to Pay Additional Fees and Annex to Form PCT/ISA/206 Communication Relating to the Results of the Partial International Search.

\* cited by examiner

*Primary Examiner*—Kevin C. Sirmons
*Assistant Examiner*—Laura C Schell
(74) *Attorney, Agent, or Firm*—Scott D. Wofsy; Edwards Angell Palmer & Dodge LLP

(57) ABSTRACT

A trocar assembly for use in surgery in a patient, comprising an elongated outer tubular member having a first or proximal end and a second or distal end. The proximal end has a housing enclosing a fluid pressure chamber therein. The distal end of the outer tubular member has a gaseous fluid discharge arrangement therethrough, through which a medical instrument is disposed for surgical manipulation of the patient.

20 Claims, 10 Drawing Sheets

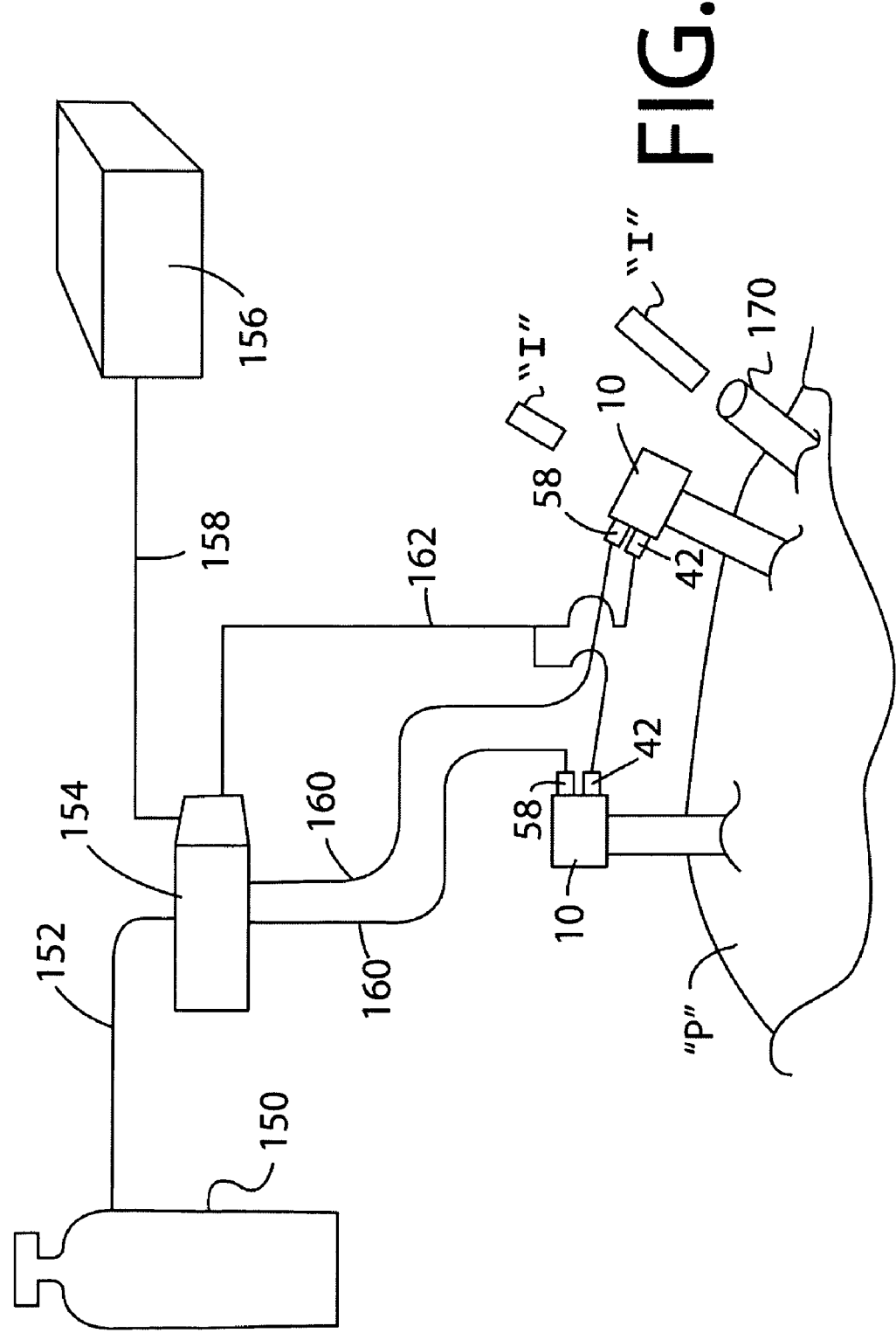

GAS FLOW TROCAR ARRANGEMENT

CROSS-REFERENCE TO RELATED APPLICATIONS

The subject application is a divisional of U.S. Patent Application Ser. No. 10/739,872, filed Dec. 18, 2003, which is now U.S. Patent No. 7,285,112, which is a continuation-in-part of U.S. Patent Application Ser. No. 10/441,149, filed May 17, 2003, which is now U.S. Patent No. 7,182,752. Each of the foregoing applications also claims the benefit of priority to U.S. Provisional Application Ser. No. 60/461,149, filed Apr. 8, 2003. Each of the foregoing applications is expressly incorporated herein by reference.

BACKGROUND OF THE INVENTION

1. Field of the Invention

This invention relates to medical devices and more particularly to access devices, and particularly their seal arrangements and closure mechanisms applicable to such medical devices.

2. Prior Art

Laparoscopic surgery is now standard procedure in hospitals today. Abdominal operations are being performed with narrow elongated instruments inserted through small incisions into interior portions of the body. Such laparoscopic procedures are now considered the treatment of choice for operations such as the removal of the gall bladder, spleen, adrenal glands, uterus and ovaries. Such laparoscopic procedures are accomplished via access through a device typically known as a trocar which facilitates the introduction of laparoscopic instruments into the abdomen of the body. The introductions of these instruments typically are done in regions which include a fluid under pressure. In the abdomen, this fluid may be a gas such as insufflation gas. It is desirable to provide for the introduction of a surgical instrument into the body cavity without permitting the reduction or loss of the operative pneumoperitoneum.

During typical laparoscopic procedures, the surgeon makes three to four small incisions, usually no larger than about twelve millimeters. These facial incisions are made with the trocar devices. The trocar makes the incision and then provides a tubular access for other instruments to be inserted into the abdominal space. The trocar also provides a means to insufflate the abdominal cavity with a low pressure gas, typically carbon dioxide, so that the surgeon has an open interior space in which to work. The trocar must provide a means to maintain the internal gas pressure with some sort of a seal between the trocar and the medical instrument he is utilizing, and still allow those surgical devices to be inserted and withdrawn. Such surgical instruments introduced through the trocar tube and into the abdomen may include scissors, grasping instruments, occluding instruments, cauterizing units, cameras, light sources and other surgical instruments.

Currently, insufflation is performed by providing a regulated pressurized gas to the peritoneal cavity via the trocar cannula. This gas, typically carbon dioxide, is supplied to a connection on the side of the trocar tube by a flexible hose thereattached. The medical instrument going through the trocar or innermost tube thereof, should be sealed relative to the trocar so that insufflation gas will not escape from the patient.

Sealing mechanisms are utilized within the trocar to prevent the escape of fluid. Such mechanisms said typically comprised an aperture or septum valve which has functioned to form a seal around the outer surface of the instrument positioned and moved within the trocar or access device. When the instrument is inserted, or is removed, the hole in the seal contracts to restrict outward gas flow. Such seals usually accept a range of instrument diameters and usually do not totally restrict outward gas flow when these instruments are retracted. Other types of valves and seals include flapper valves or trap type doors which are spring loaded. When a instrument penetrates the trocar tube access device the instrument pushes the door open. However when the instrument is retracted, such a trap door or valve may interfere with the removal of the instrument or any tissue being transported thereby.

Certain problems arise with the types of seals utilized in these trocar devices. Certain seals only work for a limited range of instrument diameters. Certain other seals inhibit the motion of the instrument as it is being inserted or as it is being withdrawn from the trocar. Typically the seals do not last through any procedures because they are subject to wear and tearing. Those prior art seals also may often interfere with the removal of the instrument and/or any tissue being withdraw from the patient utilizing that particular instrument.

It is an object of the present invention to overcome the disadvantages of the prior art.

It is a further object of the present invention to provide a seal which will work with a wide range of instrument sizes, shapes and diameters.

It is a further object of the present invention to provide a universal trocar seal for use without the seal interfering with or touching any instrument utilized therewith.

It is still yet a further object of the present invention to provide a seal which will eliminate any motion restriction for those instruments inserted therethrough, and permit improved tactile feedback to the surgeon.

It is yet a further object of the present invention to provide a seal which may be automatic in its function, as well as being controllable and adjustable, by or according to the needs of the attending surgeon.

It is a further object of the present invention to provide a path for exiting liquid and gas and a collection arrangement therefore, with a prevention of any splash therewith.

It is still yet a further object of the present invention to provide a seal which will not interfere with the removal of tissue from the interior of a body cavity as it moves through the trocar.

It is still yet a further object of the present invention to allow instruments with an irregular outside surface configuration to still maintain a seal with the trocar.

It is yet another object of the present invention to allow an instrument and a trailing suture to be utilized as in a surgical procedure such as a Nissen fundal placation.

It is yet a further object of the present invention to permit the use of two or more instruments with a combined OD less than the ID of the cannula wherein one instrument could be used for grasping and stabilizing tissue the other instrument used for cutting that stabilized tissue or cannulation (cholangiogram) of a ductal tissue without the loss of gas or the use of a further trocar.

It is a further object of the present invention to provide an arrangement for securing a trocar assembly at a surgical site and for assisting in returning that site to closure.

It is a further object of the present invention to provide a means for illuminating an abdominal site during a procedure using a trocar.

BRIEF SUMMARY OF THE INVENTION

The present invention comprises a gas flow trocar arrangement to permit the introduction of a surgical instrument and its access to the peritoneum using the flow of a fluid as the primary sealing means. The trocar arrangement of the present invention comprises an elongated device having a proximal or first end, and a distal end or second end. The proximal end comprises a cylindrically shaped housing, having an open proximal end and a shaped distal end of the housing of reduced diameter. The distal end of the housing is preferably unitarily manufactured with a generally cylindrically shaped, elongated outermost tube. The outer tube has a distal end which may comprise the distal end of the trocar assembly. The proximal housing of the trocar assembly has a proximal shoulder arranged internally thereon, adjacent its proximalmost end. The housing also has a second inner shoulder arranged thereon, adjacent the distal end of the housing.

An inner tube is arranged to be seated within the distalmost end of the proximal housing. The elongated inner tube has a first end with an annular radially outwardly extending flange, and has a distalmost end extending distal of the distal end of the outer tube. The outer tube and the inner tube are spaced apart to define an elongated, annular, fluid conducting chamber therebetween. The annular flange of the inner tube rests on the distal second shoulder arranged adjacent to the distal end of the proximal housing. An annular plenum is arranged between the distal end of the proximal housing and the annular flange. The annular plenum defines a sensing pressure chamber which is in fluid communication with the annular fluid conducting chamber arranged between the inner tube and the outer tube. A pressure sensing port is arranged in fluid communication with the annular pressure chamber plenum in the distal end of the proximal housing. The pressure sensing port is thus in fluid communication with the distalmost end of the trocar assembly which distalmost end is located within the abdomen of the patient, during the use of the trocar assembly.

A baffle insert arrangement is introducable within the proximal housing, and has a proximalmost annular flange which rests upon the proximal shoulder in the proximal housing. The baffle insert is comprised of a plurality of longitudinally spaced apart annular disks surrounding an elongated centralmost tube. A plurality of baffle ports are arranged circumferentially in the wall of the tube of the baffle insert. An annular insufflation chamber is arranged within the proximal housing and radially outwardly of the elongated bore of the baffled insert. The distalmost end of the baffle insert comprises a nozzle tube. An insufflation port is in fluid communication with the insufflation chamber radially outwardly of the nozzle tube. An annular gap is arranged between the distalmost end of the nozzle tube and the central bore of the elongated inner tube, so as to direct pressurized fluid from a pressure source, through an insufflator and a conduit, thence through the elongated annular channel/gap and into the patient and around any surgical device(s) inserted into the patient through the central nozzle tube. A resilient valve, such as a duckbill valve, for example, may be arranged within the inner side of the central inner tube along any longitudinal point thereof.

In use of the trocar assembly, one or more such surgical instruments are inserted through the longitudinal bore of the baffle insert, and into the bore extending through the inner tube. Such a surgical instrument(s) would extend between the lips or flap proportion of any resilient valve arranged within the nozzle tube, the baffle tube or the proximal end of the housing.

A positive flow of insufflation fluid such as carbon dioxide would be directed through the insufflation port on the proximal housing, and pass within the annular plenum thereadjacent. Such insufflation air would be directed out of the insufflation chamber through the annular nozzle on the distal end of the nozzle tube on the distal end of the baffle insert. Thus the continuous gas flow would act as a seal and maintain pressure within the peritoneum of the patient being operated upon, as recited in our co-pending aforementioned patent application. The elongated annular chamber, defined as the space between the outer tube and the inner tube returns a pressure-sensing gas out through the pressure-sensing port to the insufflation producing arrangement in fluid communication with the trocar assembly. Such insufflation arrangement will be discussed in further detail herein below.

In a further embodiment of the valve assembly for the maintenance of pressure within the patient being operated upon, a cap may be arranged over the proximal end of the proximal housing of the trocar assembly. Such a cap would include a central opening across which a resilient duckbill or flap type valve is disposed. A surgical instrument or instruments would thus be inserted in a sealing type manner through such a flap or duckbill valve and through the central bore of the baffle insert and the elongated coaxially disposed tubes on the distalmost end of the trocar assembly. Such surgical instrument(s) may be non-circular in cross-section because the nature of the constant gas flow seal around the instrument(s) inserted through the trocar assembly. The baffle insert in a preferred embodiment, includes the nozzle tube arranged on the distalmost end thereof being nestable within the proximal housing, and defining an annular nozzle between the distalmost end of the baffle insert and the annular opening of the radially outwardly extending annular flange on the proximal end of the innermost tube.

In a further embodiment of the baffle insert, the nozzle tube may extend distally beyond the annular flange of the inner tube, and actually internally within the inner tube in a stepped diameter inwardly, having a distalmost end anywhere within the elongated inner tube. A further annular chamber may thus be disposed between the elongated nozzle tube and the inner tube.

An arrangement of angularly arranged openings or jets may be arranged at any spaced apart location distributed longitudinally or otherwise within the elongated nozzle tube. In a further embodiment of the resilient valve, such valve would thus be arranged within the internal surface of the extended nozzle tube. Such resilient valve may be upstream or downstream longitudinally of the array of insufflation ports in the nozzle tube.

The insufflation arrangement for the trocar assembly of the present invention in the first embodiment may be comprised of a high pressurized source of carbon dioxide connected through a high pressure conduit, to an insufflator. A further high-pressure line extending from the first high-pressure line is in fluid communication with a bias control regulator valve arrangement. The bias control regulator valve arrangement has a fluid conduct conduit extending in communication with an insufflation fluid supply conduit extending from the insufflator, which is in fluid communication with an insufflation port of each respective trocar utilized in a patient being operated upon. A return line pressure sensing conduit is arranged in fluid communication with the pressure sensing return port in each respective trocar utilized on the patient, the return line in fluid communication with the bias control regulator valve arrangement.

A further insufflation arrangement for pressure balancing thereof is contemplated by a high pressure carbon dioxide source in fluid communication through a high-pressure fluid supply line conduit, with an insufflator. The high-pressure fluid supply line conduit is also in fluid communication with a regulator. The regulator is in fluid communication, through a conduit, to a pressure balance regulator. The insufflator is in fluid communication through a conduit, to the pressure balance regulator. A conduit directing insufflation fluid extends from the pressure balance regulator to the insufflation ports on each respective trocar in use with a patient. A return line conduit for pressure sensing is arranged in fluid communication with each pressure-sensing port on each trocar in use with a patient. The pressure line conduit extends and is in fluid communication with the pressure balance regulator. Such a control arrangement provides feedback to the insufflator to provide sufficient constant flow of air to any particular trocar being utilized with that patient.

A yet further embodiment of the insufflation arrangement comprises a high-pressure supply of insufflation gas such as carbon dioxide through a high-pressure supply conduit in fluid communication with an electro-pneumatic transducer having a control and display arrangement therewith. The transducer has an insufflation fluid supply conduit in communication with the respective pressure fluid receiving insufflation ports on each respective trocar utilized with a patient. A return pressure sensing fluid conduit has a fluid communication with the pressure-sensing port on each trocar and with the transducer in the insufflation supply arrangement.

A yet still further insufflation supply arrangement is comprised of a high pressure gas such as carbon dioxide in communication through a high-pressure supply conduit with a pilot valve assembly. An insufflator is also in fluid communication with the pilot valve arrangement. An insufflation supply conduit from the pilot valve is in fluid communication with the insufflation port on each particular trocar being utilized with the patient. A return pressure sensing conduit is in fluid communication with at least one trocar being utilized with the patient, that pressure-sensing conduit in fluid communication with the pilot valve. Existing insufflators may thus be utilized to monitor the insufflation pressure within the abdomen of a patient being operated upon, and the control of the flow of fluid from the insufflator will be amplified by the pilot valve through an air operated volume booster, to control the flow of insufflation gas to the high pressure insufflation port of the trocar.

The invention thus comprises a trocar assembly for use in surgery in a patient, comprising an elongated outer tubular member having a first or proximal end and a second or distal end. The proximal end may have a housing enclosing a fluid pressure chamber therein. The distal end of the outer tubular member may have a gaseous fluid discharge arrangement therethrough, through which a medical instrument is disposed for surgical manipulation of the patient. The pressure chamber in the proximal end of the outer tubular member is in fluid communication with the gaseous discharge arrangement on the distal end of the outer tubular member.

A fluid return conduit is preferably arranged between the distal end of the trocar assembly and the proximal end of the trocar assembly. The gaseous discharge arrangement provides a gaseous seal to any surgical instrument extending through the trocar assembly. A pressure sensor is in fluid communication with the fluid return conduit of the trocar assembly. A baffle is preferably arranged within the outer tubular member to function as a sound reducer in the outer tubular member. The baffle has a first tubular member extending distally therefrom to function as a guide for a medical instrument extending therethrough.

A flexible gaseous sealing valve is preferably arranged within the outer tubular member to seal any medical instrument extending therethrough. A flexible gaseous sealing valve may be arranged on the proximal end of the elongated outer tubular member. The housing preferably includes a return gaseous fluid receiving chamber. The outer tubular member of the trocar assembly in a further preferred embodiment may be non-circular (for example, an oval, a narrow rectangle or the like) to minimize trauma to the surgical incision in the patient being operated upon. Such non-circular cross-sectional shape of the trocar assembly may also permit the use of such trocar assembly with surgical instruments of non-circular cross-sectional shape, such as for example, stitching devices, staplers, retrievers or graspers, either alone or in simultaneous combined use of several surgical instruments in the same trocar assembly. Such multiple instruments may now be designed to accommodate simultaneous use in a trocar assembly of the present invention. The prior art did not permit such combination because of the sealing limitations of such prior art trocars when even a single instrument extended through the prior art trocar.

The gaseous fluid receiving chamber is preferably in fluid communication with an insufflation fluid supply arrangement. The fluid pressure chamber is preferably in fluid communication with an insufflation fluid supply arrangement. The gaseous fluid receiving chamber and the fluid pressure chamber each preferably have a port in communication with an insufflation arrangement to provide and control pressure and provide a gaseous seal relative to the trocar assembly utilized in a patient. A pressurized fluid supply is preferably in fluid communication with the fluid pressure chamber to provide a pressurized sealing fluid about a surgical instrument extending through the trocar assembly and to provide a balanced fluid supply to maintain a proper pneumoperitoneum for the patient being operated upon.

The invention may also comprise a method of maintaining the pneumoperitoneum of a surgical patient during a surgical operation, comprising the steps of: inserting a trocar assembly into a site on the patient; providing a constant gas pressure to a port on the trocar assembly, inserting at least one surgical instrument through a central channel in the trocar assembly; and sealing the instrument with respect to the trocar assembly by a jet of gaseous fluid being directed through the trocar and about the instrument, returning the gaseous fluid from the patient out a return channel in the trocar assembly, monitoring the returning gaseous fluid from the patient for pressure, flow rates, temperature, moisture or composition, inserting a flexible valve on or in the central channel to seal the instrument and minimize undesired leakage of gaseous fluid from the patient. The jet of gaseous fluid may be directed about the instrument in the central channel at any longitudinal location of that instrument in the central channel. The trocar assembly preferably has an inner channel which is removable from the trocar assembly.

The invention may also comprise a method of maintaining the pneumoperitoneum of a patient during a surgical procedure utilizing a trocar assembly, comprising one or more of the following steps: inserting a trocar through an incision in the patient; inserting a surgical instrument through said trocar assembly and into the patient; providing a pressurized fluid through the trocar; sealing the instrument with a flow of the pressurized fluid to maintain the pneumoperitoneum and provide a sealing of the instrument extending therethrough; inserting a further instrument through the trocar assembly and into the patent being operated upon.

The instrument may be in another preferred embodiment be non-circular in cross-section along at least a portion thereof extending through the trocar assembly. The trocar assembly may in another preferred embodiment have an outer tubular member of non-circular cross-section along a portion thereof which extends into the patient being operated upon.

BRIEF DESCRIPTION OF THE DRAWINGS

The objects and advantages of the present invention will become more apparent when viewed in conjunction with the following drawings, in which:

FIG. 9 is a schematic representation of a further embodiment of an insufflation system to be utilized with a trocar of the present invention.

DETAILED DESCRIPTION OF THE PREFERRED EMBODIMENTS

Figure 1:
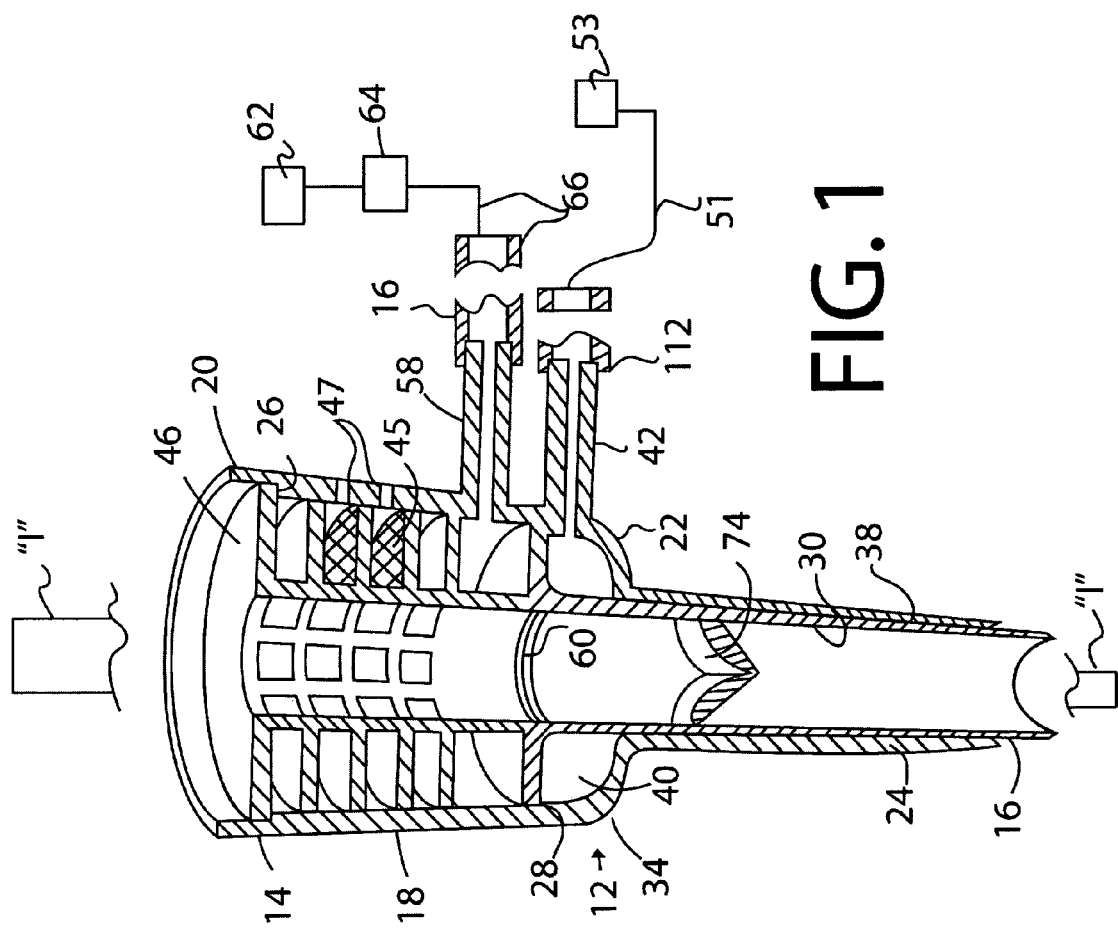
FIG. 1 is a side-elevational view, in section, of a trocar assembly, showing a portion of a surgical instrument extending therethrough.

Referring now to the drawings in detail, and particularly to FIG. 1, there is shown the present invention which comprises a gas flow trocar assembly 10 to permit the introduction of one or more surgical instruments "I" and its access to the peritoneum of a patient using the flow of a fluid as the primary sealing means. The trocar assembly 10 of the present invention comprises an elongated device 12 having a proximal or first end 14, and a distal end or second end 16. The proximal end 14 comprises a cylindrically shaped housing 18, shown in FIGS. 1, 2 and 5, having an open proximal end 20 and a shaped distal end 22 of the housing 18, of reduced diameter. The distal end 22 of the housing 18 is preferably unitarily manufactured with a generally cylindrically (in one embodiment) shaped, elongated outer tube 24. The outer tube 24 has a distal end which may comprise the distal end 16 of the trocar assembly 10. The proximal housing 18 of the trocar assembly 10 preferably has a proximal shoulder 26 arranged internally thereon, adjacent its proximalmost end 14. The housing 18 may also preferably have a second inner shoulder 28 arranged thereon, adjacent the distal end 22 of the housing 18.

Figure 2:
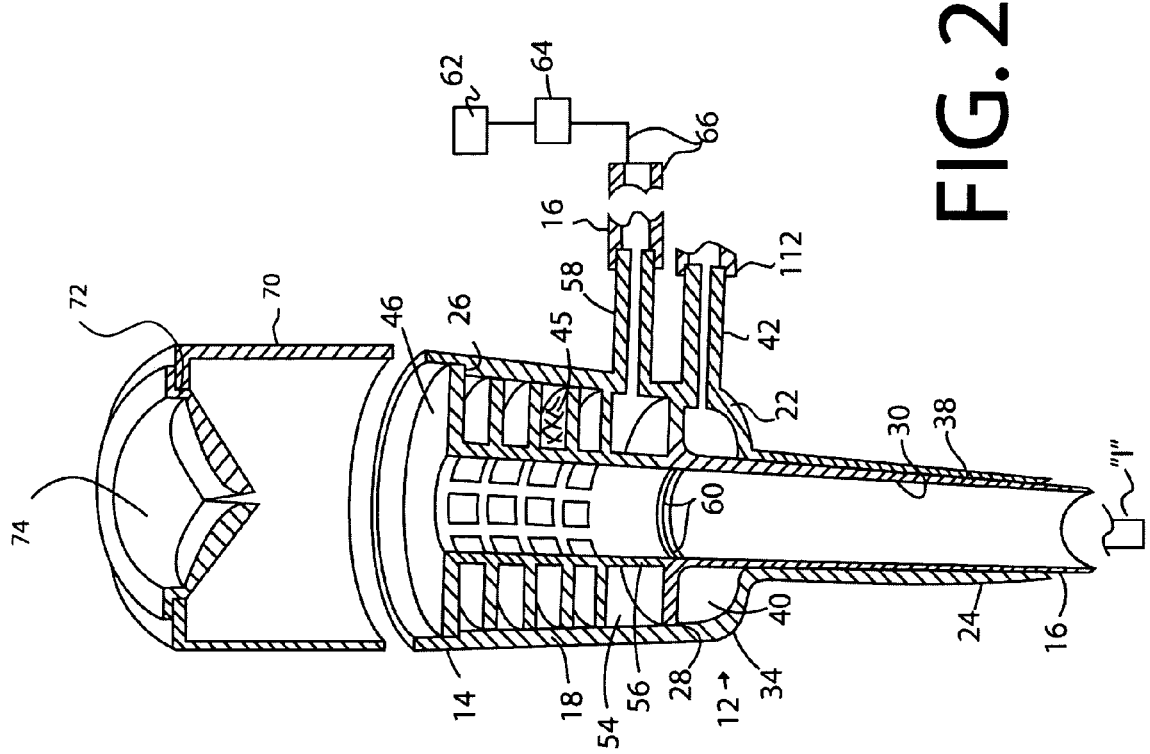
FIG. 2 is a view similar to FIG. 1, showing a further embodiment of a valve arrangement to be utilized with the trocar assembly.
Figure 4:
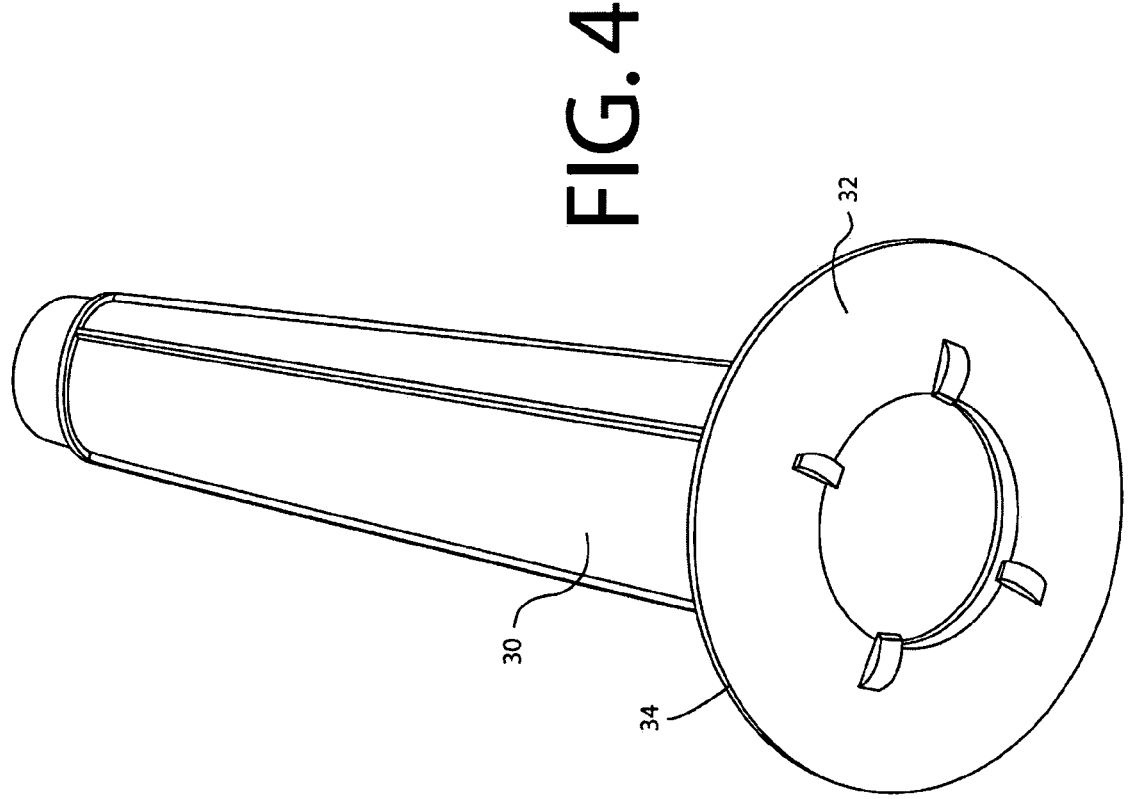
FIG. 4 is a perspective view of the inner tube of the trocar assembly of the present invention.

An inner tube 30, shown more clearly in FIG. 4, is arranged to be seated within the distalmost end 22 of the proximal housing 18, as is shown in FIGS. 1 and 2. The elongated inner tube 30 has a first end 32 with an annular radially outwardly extending flange 34, and has a distalmost end 36 which may extend distal of the distal end of the outer tube 16, as may be seen in FIG. 1. The outer tube 24 and the inner tube 30 are spaced radially apart to define an elongated, annular, fluid conducting chamber 38 arranged there-between, as may be seen more clearly in FIG. 5. The annular flange 34 of the inner tube 30 rests on the distal second shoulder 28 arranged adjacent to the distal end 22 of the proximal housing 18, as is represented in FIGS. 1 and 2. An annular plenum 40 is arranged between the distal end 22 of the proximal housing 18 and the annular flange 34. The annular plenum 40 defines a sensing pressure chamber which is in fluid communication with the annular fluid conducting chamber 38 arranged between the inner tube 30 and the outer tube 24. A pressure sensing port 42 is arranged in fluid communication with the annular pressure chamber plenum 40 in the distal end of the proximal housing 18. The pressure sensing port 42 is thus in fluid communication with the distalmost end 16 of the trocar assembly 10 which distalmost end 16, is located within the abdomen of the patient, during the use of the trocar assembly 10, as represented in FIG. 6 et seq.

Figure 3:
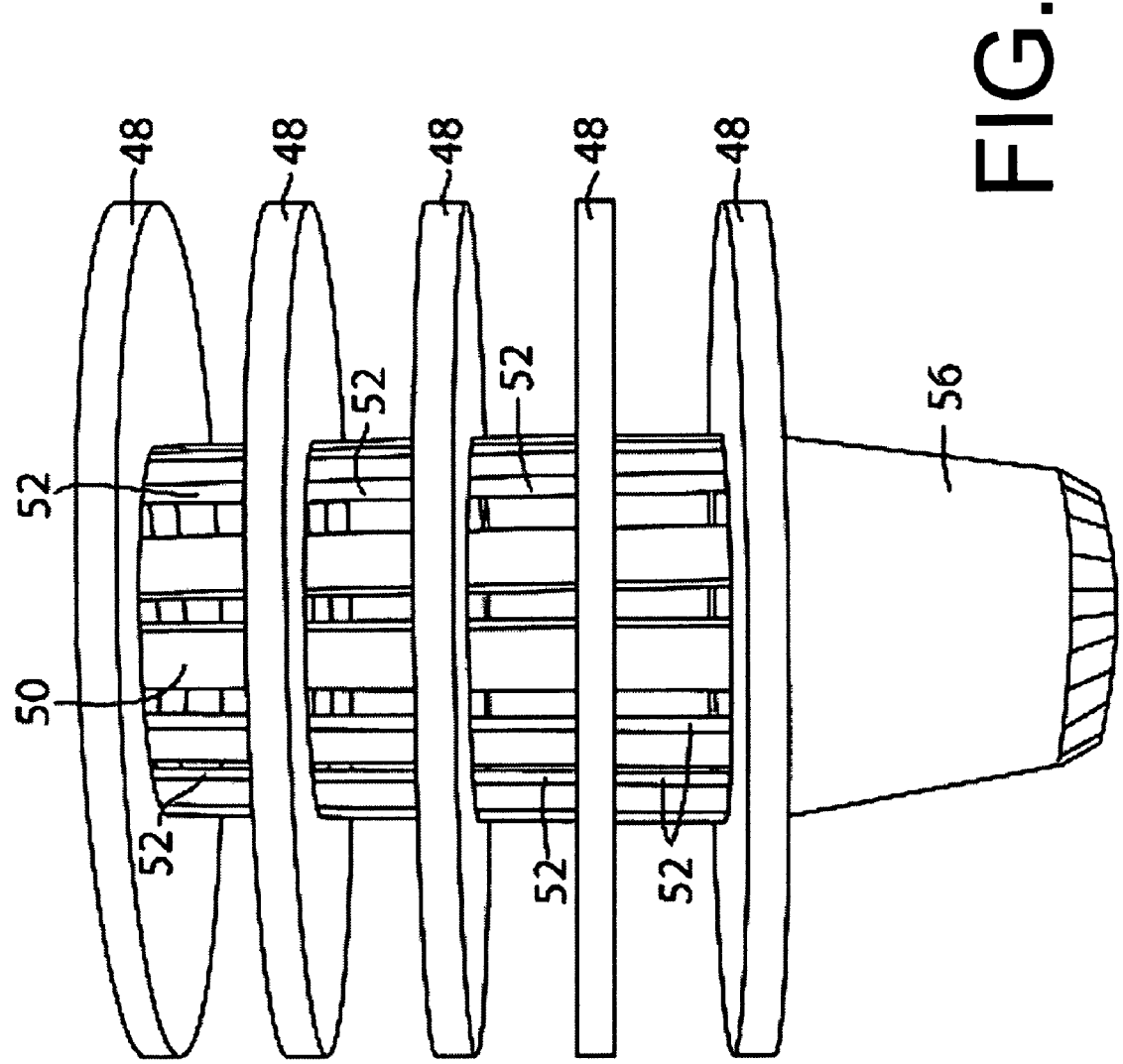
FIG. 3 is a side-elevational view of a baffle insert as part of the trocar assembly.

A baffle insert arrangement 44, shown by itself in FIG. 3, is introducable within the proximal housing 18, and has a proximalmost annular flange 46 which rests upon the proximal shoulder 26 in the proximal housing 18, as is represented in FIGS. 1 and 2. The baffle insert 44 is preferably comprised of a plurality of longitudinally spaced apart annular disks 48 surrounding an elongated centralmost tube 50. The baffle insert 44 may in a further embodiment have a porous filter 45 arranged in a proximal portion thereof, as represented in FIG. 1. Such an embodiment may include a plurality of exhaust openings 47 arranged through the sidewall of the housing 18, as represented in FIGS. 1 and 2. Such openings 47 may be directed to a further conduit, not shown for clarity, for recycling of exhausted gaseous fluid into the atmosphere or into the patient's insufflator system 53.

In one preferred embodiment, a plurality of baffle ports 52 are arranged circumferentially in the wall of the tube 50 of the baffle insert 44. An annular insufflation chamber 54 is arranged within the proximal housing 14 and radially outwardly of the elongated tube 50 of the baffled insert 44. The distalmost end of the baffle insert 44 comprises a nozzle tube 56. An insufflation port 58 is in fluid communication with the insufflation chamber 54 radially outwardly of the nozzle tube 56. An annular gap 60 is arranged between the distalmost end of the nozzle tube 56 and the central bore of the elongated inner tube 30, so as to direct pressurized fluid from a pressure source 62, as will be described hereinbelow, through an insufflator 64, and a conduit 66, thence through the elongated annular channel/gap 60 and into the patient and around any surgical device(s) "I" inserted into the patient through the central nozzle tube 30. A resilient valve 68, such as a duckbill valve, for example, as represented in FIG. 1, may be arranged within the inner side of the central inner tube 30 along any longitudinal point thereof.

In use of the trocar assembly 10, one or more such surgical instruments "I" may be inserted through the longitudinal bore of the baffle tube 50 and 56, and into the bore extending through the elongated inner tube 30. Such a surgical instrument(s) "I" would extend between the lips or flap proportion of any resilient valve 68 arranged within the nozzle tube 30, the baffle tube 50 or 56, or the proximal end of the housing 14.

In a further embodiment of the valve assembly for the maintenance of pressure within the patient being operated upon, a cap 70 may be removably arranged over the proximal end of the proximal housing 14, as represented in FIG. 2 of the trocar assembly. Such a cap 70 would include a central opening 72 across which a resilient duckbill or flap type valve 74 is disposed. A surgical instrument or instruments "I" may thus be sealably inserted through such a flap or duckbill valve 74 and through the central bore of the baffle insert and the elongated coaxially disposed tubes on the distalmost end of the trocar assembly 10. Such surgical instrument(s) "I" may be non-circular in cross-section because the nature of the constant gas flow seal around the instrument(s) inserted through the trocar assembly 10 permits non-circular instruments to be so utilized.

Figure 5:
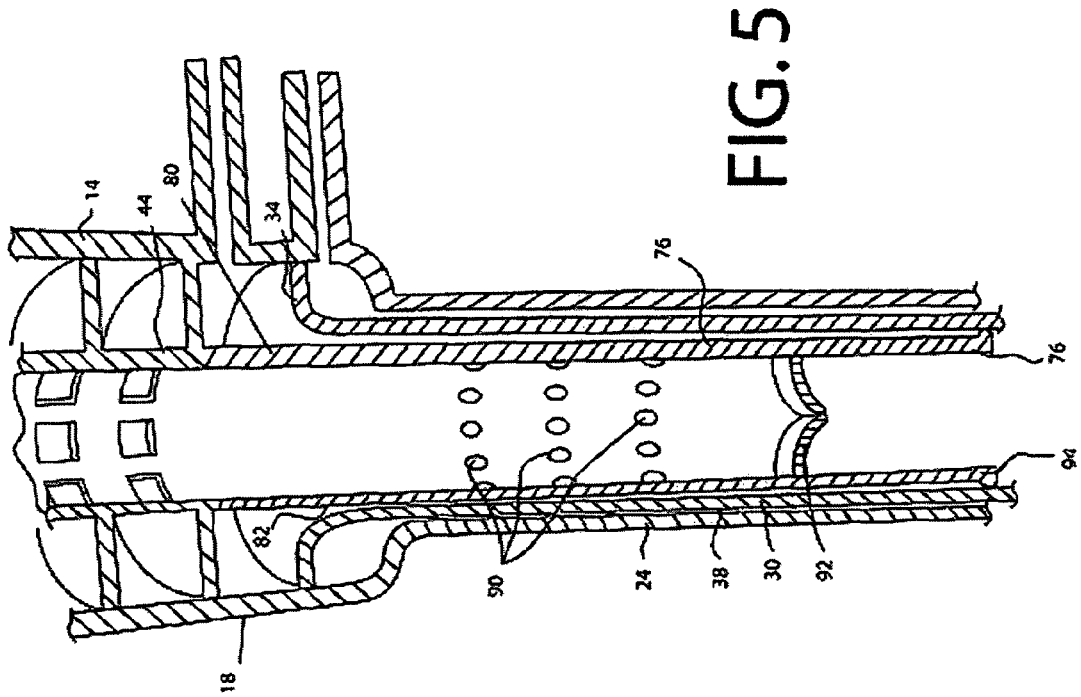
FIG. 5 is a sectional view of a portion of an extended nozzle tube as a further embodiment of a baffle insert and nozzle arrangement therewith.
Figure 5A:
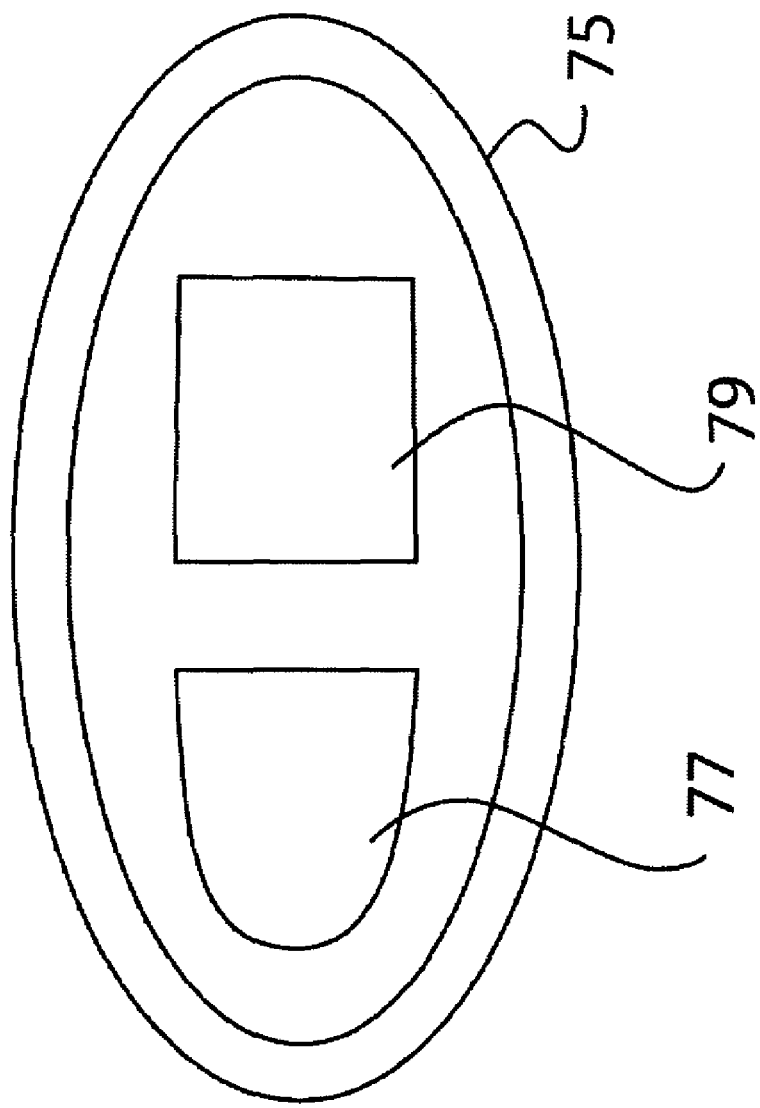
FIG. 5A is a cross-sectional view of a trocar assembly of non-circular cross-section with more then one surgical instrument extending therethrough, the instruments being of non-circular cross-section.
Figure 6:
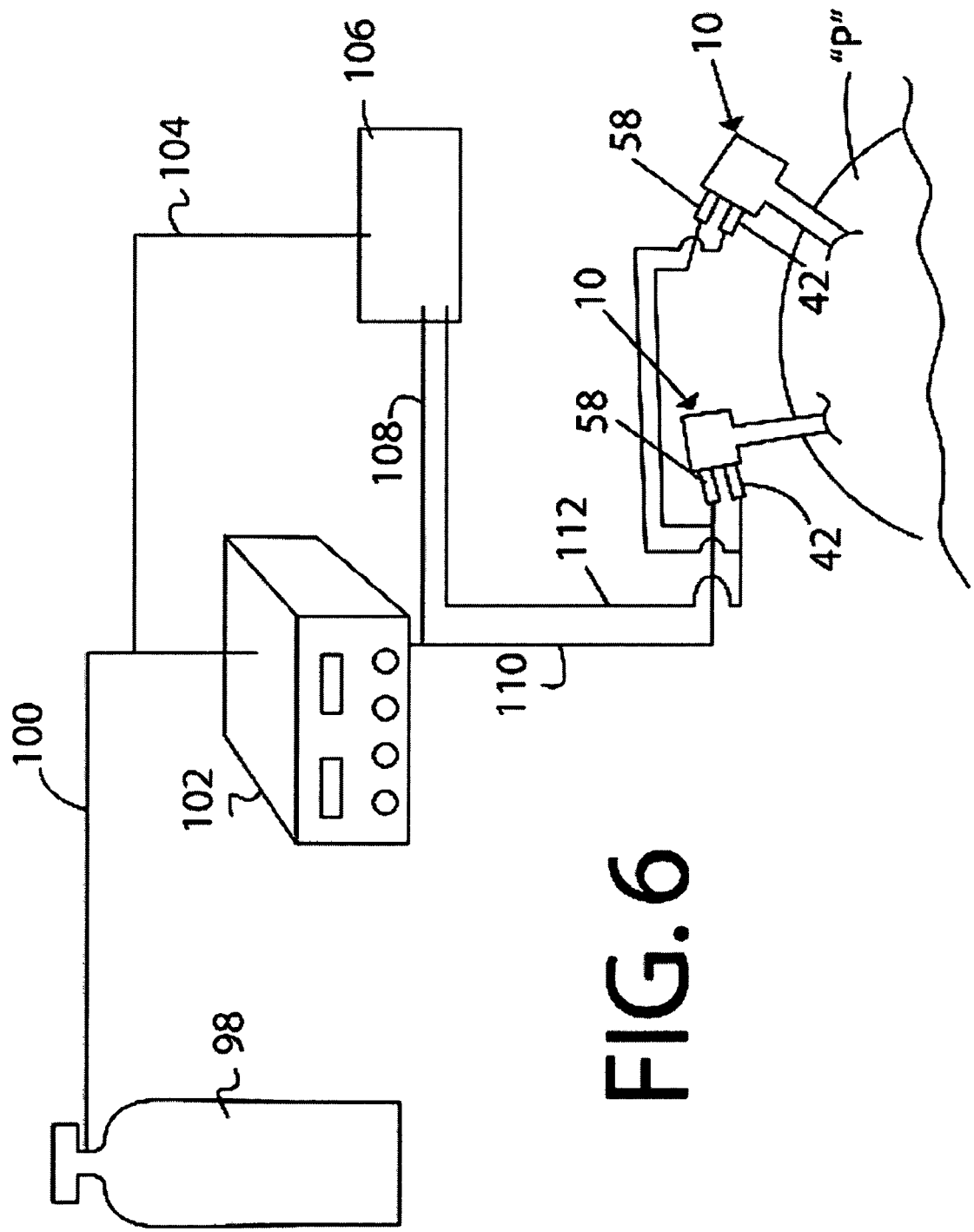
FIG. 6 is a schematic representation of an insufflation system for use with a trocar of the present invention.

The baffle insert 44 in another preferred embodiment, may for example include an extended length nozzle tube 76 arranged on the distalmost end thereof, as represented in FIG. 5, the extended nozzle tube 76 being insertable through the proximal housing 18, and defining an elongated annular channel 78 extending between the distalmost end 80 of the baffle insert and the annular opening 82 of the radially outwardly extending annular flange 34 on the proximal end of the innermost tube 38. FIG. 5A shows a trocar assembly 10 having an outer tubular member 75 on non-circular shape (such shape may be for example be oval, square, "D" shaped, rectangular or the like) to permit a surgical instrument 77 and/or 79 to be inserted therethrough, of non-circular cross-sectional shape. Such instruments 77 and 79 may be stitching devices, graspers, adhesive applicators, or the like which may not be functionally best in a circular shape. Now such shape and number of instruments 77 and 79 may be utilized simultaneously because of the sealing and splashback prevention arrangement of the present invention.

In a further embodiment of the baffle insert 44, as shown in FIG. 5, the nozzle tube 80 may extend distally beyond the annular flange 34 of the elongated inner tube 30, and extend internally within the elongated inner tube 30 in a stepped or tapered diameter inwardly, having a distalmost end 76 or 76' anywhere within the elongated inner tube 30. A further annular chamber may thus be disposed between the elongated nozzle tube 80 and the elongated inner tube 30. An arrangement of angularly arranged openings or jets 90 may be arranged at any spaced apart location distributed longitudinally or otherwise within the elongated nozzle tube 80. In a further embodiment of the resilient valve 92, such a valve 92 would thus be arranged within the internal surface of the extended nozzle tube 80, as represented in FIG. 5. Such resilient valve 92 may be upstream or downstream longitudinally of the array of insufflation ports 90 in the nozzle tube 80. An annular seal 94 may preferably be arranged at the distal end of the extended nozzle tube 80 and the end of the extended inner tube 30, as represented in FIG. 5, to insure that the pressurized gaseous fluid from the annular plenum chamber 40 surround and provides the proper barrier for any instrument(s) extending and working in a patient's abdomen through the extended inner tube 30.

A positive flow of insufflation fluid such as carbon dioxide would be directed through the insufflation port 58 on the proximal housing 18, and pass within the annular plenum 54 thereadjacent. Such insufflation fluid would be directed out of the insufflation chamber plenum 58 and axially through the annular nozzle 60, (in one preferred embodiment) on the distal end of the nozzle tube 56 on the distal end of the baffle insert 44. Thus the continuous gas flow would act as a seal and maintain balanced fluid pressure within the peritoneum of the patient being operated upon, by being monitored through the pressure sensing port 42 and its fluid communication line 51 extending to the regulation means 53, as recited in our co-pending aforementioned patent application. The elongated annular chamber 38, defined as the space between the outer tube 24 and the elongated inner tube 30 returns a pressure-sensed gas out through the returning fluid gas pressure-sensing port 42 to the insufflation producing arrangement in fluid communication with the trocar assembly 10, with the majority of such gaseous fluid returning through the inner tube 30 and through the baffle arrangement 44. Such insufflation arrangement embodiments will be discussed with reference to FIGS. 6, 7, 8 and 9, in further detail hereinbelow.

The arrangement of angularly arranged openings or jets 90, as represented for example in FIG. 5, may be arranged at any spaced apart location distributed longitudinally or otherwise within the elongated nozzle tube 76'. In a further embodiment of the resilient valve 92, for example, a duckbill type valve, such valve would thus be arranged within the internal surface of the extended nozzle tube 76'. Such resilient valve may also be upstream or downstream longitudinally of the array of insufflation fluid and instrument shielding introduction ports 92 in the nozzle tube 76'.

The insufflation arrangement for the trocar assembly 10 of the present invention in the first embodiment represented in FIG. 6 may be comprised of a high pressurized source 98 comprising a tank of carbon dioxide or the like, connected through a high pressure conduit 100, and is in fluid communication with an insufflator 102. A further high-pressure line 104, extending from the first high-pressure line 100 is in fluid communication with a bias control regulator valve arrangement 106. The bias control regulator valve arrangement 106 has a fluid conduct conduit 108 extending in communication with an insufflation fluid supply conduit 110 extending from the insufflator 102, which insufflator 102 is in fluid communication with the insufflation port 58 of each respective trocar assembly 10 utilized in a patient "P" being operated upon. A return line pressure sensing conduit 112 is arranged in fluid communication with the pressure sensing return port 42 in each respective trocar assembly 10 utilized on the patient, the return line in fluid communication with the bias control regulator valve arrangement 106.

Figure 7:
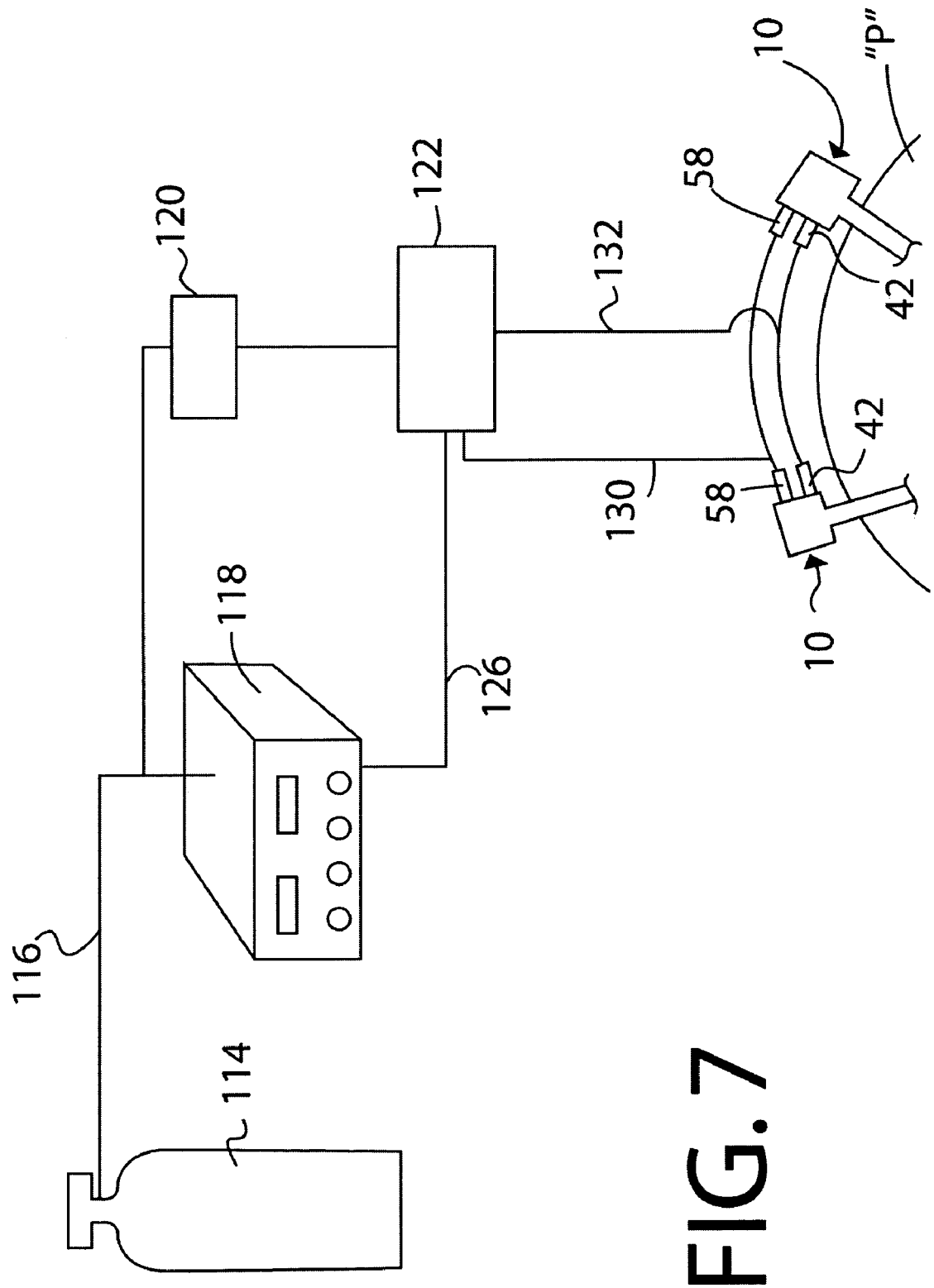
FIG. 7 is a further embodiment of the insufflation system to be utilized with a trocar of the present invention.

A further insufflation arrangement for pressure balancing thereof is contemplated, as shown for example in FIG. 7, by a high pressure carbon dioxide source 114 in fluid communication through a high-pressure fluid supply line conduit 116, with an insufflator 118. The high-pressure fluid supply line conduit 116 is also in fluid communication with a regulator 120. The regulator 120 is in fluid communication, through a conduit 122, to a pressure balance regulator 124. The insufflator 118 is in fluid communication through a conduit 126, to the pressure balance regulator 124. A conduit 130 is arranged to direct insufflation fluid from the pressure balance regulator 124 to the insufflation ports 58 on each respective trocar assembly 10 in use with a patient "P". A return line conduit 132 for pressure sensing is arranged in fluid communication with each pressure-sensing port 42 on each trocar assembly 10 in use with the patient "P". The pressure line conduit 132 extends to and is in fluid communication with the pressure balance regulator 124. Such a control arrangement provides feedback to the insufflator 118 to provide sufficient constant flow and control thereof air to any particular trocar assembly 10 being utilized with that patient 10.

Figure 8:
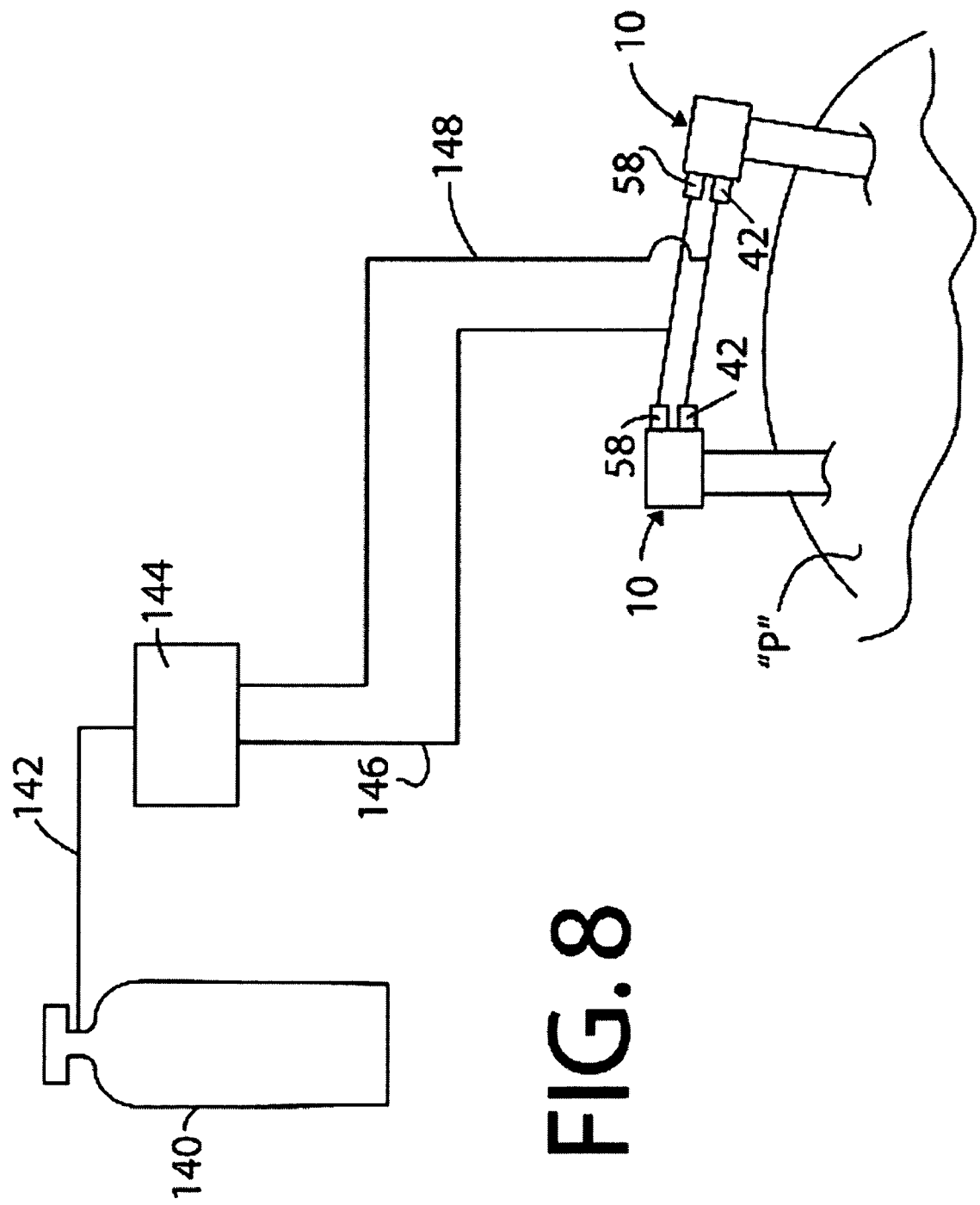
FIG. 8 is a schematic representation of the insufflation system to be utilized with a trocar of the present invention.

A yet further embodiment of the insufflation arrangement is represented in FIG. 8 which comprises a high-pressure supply of insufflation gas 140 for a gas such as for example, carbon dioxide, through a high-pressure supply conduit 142 in fluid communication with an electro-pneumatic transducer 144 having a control and display arrangement therewith. The transducer 144 has an insufflation fluid supply conduit 146 in communication with the respective pressure fluid receiving insufflation ports 58 on each respective trocar assembly 10 utilized with a patient "P". A return pressure sensing fluid conduit 148 is in fluid communication with the pressure-sensing discharge port 42 on each trocar assembly 10 and with the transducer 144 in the insufflation supply arrangement.

A yet still further insufflation supply arrangement, shown for example in FIG. 9, is comprised of a high pressure gas container 150 having a gas as for example carbon dioxide, in communication through a high-pressure supply conduit 152 with a pilot valve assembly 154. An insufflator 156 is also in fluid communication through a conduit 158 with the pilot valve assembly 154. An insufflation supply conduit 160 from the pilot valve assembly 158 is in fluid communication with the insufflation port 58 on each particular trocar assembly 10 being utilized with the patient "P". A return pressure-sensing conduit 162 is in fluid communication with at least one trocar assembly 10 being utilized with the patient "P", that pressure-sensing conduit 162 in fluid communication with the pilot valve assembly 154. Existing insufflators may thus be utilized to monitor the insufflation pressure within the abdomen of a patient "P" being operated upon, and the control of the flow of fluid from the insufflator will be amplified by the pilot valve through an air operated volume booster, to control the flow of insufflation gas to the high pressure insufflation port of the trocar; Use of a trocar assembly 10 of the present invention may also permit a regular cannula 170 to be utilized for the passage of an instrument "I" in the operative field on the patient because of the pressure maintainance feedback and pressure control of the trocar 10 with its pressure support system as represented in FIG. 6 et seq.

Thus what has been shown is a unique trocar assembly having a pressurized gas flow to provide a constant gaseous seal to an instrument or instruments utilized therethrough which simultaneously maintaining the pneumoperitoneum necessary for a laparoscopic operation as for example, on the patient's abdomen. The trocar assembly may have one or more splash resistant valves arranged at one or more locations within or at the proximal end of the innermost bore through the trocar assembly. The location of the gas fluid flow surrounding the instrument within the trocar may be introduced through an annular nozzle distally adjacent the baffle arrangement within the proximal housing, or such gas fluid flow may be introduced at a spaced apart array of jets or discharge points within an elongated central tubular extension of the baffle. The baffle, arranged within the proximal housing provides a noise reduction to the gaseous fluid being introduced in a surrounding manner to the medically operative instrument or instruments extending through the trocar assembly. Use of existing insufflator equipment is permitted by conduits in communication with regulators and valving arrangements connected to the insufflation fluid introduction port and to the return fluid gas-pressure sensing port on each respective trocar assembly to provide a balance of fluid into the patient with the fluid being discharged from the patient through the trocar assembly while limiting splashback and minimizing any fluid escape through the flexible valves disposed within the trocar assembly itself.

We claim:

1. An access device for introducing surgical instruments into a body cavity comprising:
   a) an outer tubular member having opposed proximal and distal end portions, the proximal end portion of the outer tubular member having a proximal housing associated therewith; and
   b) an inner tubular member having opposed proximal and distal end portions, the inner tubular member having a proximal flange at a proximal end thereof which is seated within the proximal housing of the outer tubular member so as to define a plenum chamber within the proximal housing of the outer tubular member above the proximal flange of the inner tubular member, wherein the plenum chamber is in fluid communication with an annular nozzle configured to direct pressurized fluid in an axial direction from the plenum chamber into a central bore of the inner tubular member to provide a constant gaseous seal around a surgical instrument inserted through the central bore of the inner tubular member while simultaneously preventing a loss of pressurized fluid from the body cavity through the central bore of the inner tubular member, and wherein the plenum chamber is adapted and configured to receive pressurized fluid and conduct the pressurized fluid to the annular nozzle.

2. An access device as recited in claim 1, wherein the proximal flange is seated within the proximal housing of the outer tubular member so as to further define a sensing chamber below the proximal flange of the inner tubular member within the proximal housing of the outer tubular member.

3. An access device as recited in claim 2, wherein the sensing chamber has an outlet port for communicating with a pressure regulator.

4. An access device as recited in claim 3, further comprising a pressure regulator in fluid communication with the outlet port of the sensing chamber.

5. An access device as recited in claim 2, wherein the sensing chamber is in fluid communication with a sensing channel defined between the inner and outer tubular members.

6. An access device as recited in claim 2, wherein a baffle is arranged within the proximal housing of the outer tubular member, proximal to the plenum chamber.

7. An access device as recited in claim 6, wherein the baffle includes a plurality of longitudinally spaced apart discs surrounding a central tube.

8. An access device as recited in claim 1, wherein the plenum chamber has an inlet port for communicating with a source of pressurized fluid.

9. An access device as recited in claim 8, further comprising a source of pressurized fluid in communication with the inlet port of the plenum chamber.

10. An access device as recited in claim 1, wherein a resilient valve is arranged within a central bore of the inner tubular member.

11. An access device as recited in claim 1, further comprising a cap removably arranged with the proximal housing portion of the outer tubular member and having a resilient valve arranged therein.

12. An access device as recited in claim 1, wherein the nozzle is defined by a gap formed between a distal end of a nozzle tube disposed within the proximal housing of the outer tubular member and the central bore of the inner tubular member.

13. An access device for introducing surgical instruments into a body cavity comprising:
   a) an outer tubular member having opposed proximal and distal end portions;
   b) an inner tubular member having opposed proximal and distal end portions; and
   c) a housing associated with the proximal end portion of the outer tubular member, the housing defining a proximal plenum chamber and a distal sensing chamber, wherein the proximal plenum chamber is in fluid communication with a nozzle axially aligned and communicating with a central bore of the inner tubular member, wherein the annular nozzle is configured to direct pressurized fluid in an axial direction from the plenum chamber into the central bore of the inner tubular member to provide a constant gaseous seal around a surgical instrument inserted through the central bore of the inner tubular member while simultaneously preventing a loss of pressurized fluid from the body cavity through the central bore of the inner tubular member, wherein the proximal plenum chamber is adapted and configured to receive pressurized fluid and conduct the pressurized fluid to the annular nozzle and wherein the distal sensing chamber is in fluid communication with a sensing channel formed between the inner and outer tubular members communicating with the body cavity.

14. An access device as recited in claim 13, wherein the plenum chamber has an inlet port communicating with a source of pressurized fluid.

15. An access device as recited in claim 13, wherein the sensing chamber has an outlet port communicating with a pressure regulator.

16. An access device as recited in claim 13, wherein a baffle is arranged within the housing proximal to the plenum chamber.

17. An access device as recited in claim 13, wherein the baffle includes a plurality of longitudinally spaced apart discs surrounding a central tube.

18. An access device as recited in claim 17, wherein the nozzle is defined by a gap formed between a distal end of the central tube of the baffle and the central bore of the inner tubular member.

19. An access device as recited in claim 13, wherein a resilient valve is arranged within a central bore of the inner tubular member.

20. An access device as recited in claim 13, further comprising a cap removably arranged with the proximal housing portion of the outer tubular member and having a resilient valve arranged therein.

* * * * *